(12) United States Patent
Lin et al.

(10) Patent No.: US 6,197,554 B1
(45) Date of Patent: Mar. 6, 2001

(54) METHOD FOR GENERATING FULL-LENGTH CDNA LIBRARY FROM SINGLE CELLS

(76) Inventors: Shi-Lung Lin, 731 S. Chapel Ave. #F, Alhambra, CA (US) 91801; Cheng-Ming Chuong, 4 Bergamo, Irvine, CA (US) 02614; Shao-Yao Ying, 1953 Wellesley Rd., San Marino, CA (US) 91108

(*) Notice: Subject to any disclaimer, the term of this patent is extended or adjusted under 35 U.S.C. 154(b) by 0 days.

(21) Appl. No.: 09/197,951

(22) Filed: Nov. 20, 1998

(51) Int. Cl.[7] .................................................. C12P 19/34
(52) U.S. Cl. .............................. 435/91.1; 435/6; 435/15; 435/91.21; 435/91.2; 435/91.5; 435/91.51; 536/23.1; 536/24.1; 536/25.3; 935/18; 935/19; 935/93; 935/16
(58) Field of Search .......................... 435/91.1, 6, 15, 435/91.21, 91.2, 91.5, 91.51; 536/23.1, 24.1, 25.3; 935/18, 19, 93, 16

(56) References Cited

U.S. PATENT DOCUMENTS

| | | | |
|---|---|---|---|
| 5,021,335 | * 6/1991 | Tecott et al. | 435/6 |
| 5,482,854 | 1/1996 | O'Leary | 435/283.1 |
| 5,514,545 | * 5/1996 | Eberwine et al. | 435/6 |
| 5,637,685 | 6/1997 | Soares | 536/23.1 |
| 5,702,898 | 12/1997 | Bonaldo | 435/6 |
| 5,932,451 | * 8/1999 | Wang et al. | 435/91.21 |

OTHER PUBLICATIONS

Jacques Mallet et al, "Oligodeoxyribonucleotide ligation to single–stranded cDNAs", Nucleic Acid Research. vol. 19. No. 19 5227–5232.

Shi–Lung et al, "In vivo analysis of cancerous gene expression by RNA–polymerase chain reaction", Oxford University Press, Nucleic Acids Research, 1999, vol. 27, No. 23 4585–4589.

(List continued on next page.)

*Primary Examiner*—Kenneth R. Horlick
*Assistant Examiner*—Janell Taylor
(74) *Attorney, Agent, or Firm*—Raymond Y. Chan; David and Raymond

(57) ABSTRACT

The present invention provides a fast, simple and specific method for generating a complete full-length cDNA library from single cells. The first reverse transcription of intracellular mRNAs with an oligo(dT)n-promoter primer introduces a recognition site for following transcription of newly reverse-transcribed cDNAs. The poly-nucleotide tailing of above cDNAs in addition to aforementioned promoter region further forms binding templates for specific PCR amplification. After repeating the reverse transcription, transcription, reverse transcription and PCR procedure, we can multiply a single copy of mRNA to two billion folds by calculation based upon the comparison between the amount of a synthesized cDNA library and that of theoretically presumed mRNAs within a cell (0.1 pg). In conjunction with a cell fixation and permeabilization step, the complete full-length cDNA library can be directly generated from few single cells without mRNA degradation. The present invention will be very useful in preparing tissue-specific full-length cDNA libraries for future gene chip technology.

44 Claims, 2 Drawing Sheets

OTHER PUBLICATIONS

Shi–Lung Lin et al, "Generation of Full–Length cDNA Library from Single Human Prostate Cancer Cells", Bio-Techniques, p410–414 (Sep. 1999).

Sambrook et al., "Molecular Cloning, 2nd Ed.", Cold Spring Harbor Laboratory Press, pp8.11–8.35 (1989).

Patanjeli et al., "Constructionon of a uniform abundance (normalized) cDNA library", Proc. Natl. Acad. Sci. USA 88: 1943–1947 (1991).

O'Dell et al., "Amplification mRNAs from Single, Fixed, Tunel–Positive Cells", Biotechniques 25: 566–570 (1998).

Eberwine etal. "Analysis of gene expression in single live neutrons". Proc. Natl. Acad. Sci. USA 89: 3010–3014 (1992).

Crino et al. "Embryonic neutronal markers in tuberous sclerosis: Single–Cell Molecular Pathology", Proc. Natl. Acad. Sci. USA 93: 14152–14157 (1996).

Embleton Et al., "In–cell PCR from mRNA: amplifying and linking the rearranged immunoglobulin heavy and light chain V–genes within single cells", Nucleic Acid Re. 20: 3831–3837 (1992).

* cited by examiner

METHOD FOR GENERATING FULL-LENGTH CDNA LIBRARY FROM SINGLE CELLS

BACKGROUND OF THE INVENTION

1. Field of The Invention

The present invention generally relates to the field of methods for generating full-length complementary DNA library from single cells. More particularly, the present invention relates to the field of novel methods of complete full-length cDNA library synthesis from as few as a cell.

2. Description of The Prior Art

The following references are pertinent to this invention:

1. Sambrook et.al., "*Molecular Cloning*, 2nd Edition", Cold Spring Harbor Laboratory Press, pp8.11–8.35 (1989).
2. Patanjeli et.al., "Construction of a uniform abundance (normalized) cDNA library", *Proc. Natl. Acad. Sci. USA* 88: 1943–1947 (1991).
3. O'Dell et.al., "Amplification of mRNAs from Single, Fixed, TUNEL-Positive Cells", *BioTechniques* 25: 566–570 (1998).
4. Eberwine et.al, "Analysis of gene expression in single live neurons", *Proc. Natl. Acad. Sci. USA* 89: 3010–3014 (1992).
5. Crino et.al., "Embryonic neuronal markers in tuberous sclerosis: Single-Cell Molecular Pathology", *Proc. Natl. Acad. Sci. USA* 93: 14152–14157 (1996).
6. Embleton et.al, "In-cell PCR from mRNA: amplifying and linking the rearranged immunoglobulin heavy and light chain V-genes within single cells", *Nucleic Acid Res.* 20: 3831–3837 (1992).
7. U.S. Pat. No. 5,482,854 issued to Soares et.al.
8. U.S. Pat. No. 5,637,685 issued to Soares et.al.
9. U.S. Pat. No. 5,702,898 issued to Bonaldo et.al.

The ability to generate complete complementary DNA (cDNA) library from gene transcripts of single cells has permitted the molecular investigations of intracellular gene expressions under certain special conditions, such as pathogenesis, mutation, treatment processing and developmental control. Because the formation of a full-length cDNA library requires reverse transcription of every messenger RNA (mRNA) in a cell without degradation, the content of this library preserves the whole gene expression repertoire of the cell under tested condition. When single cells from tissue are used, the full-length cDNA library will represent the tissue-specific gene expression pattern and can be used to test differentially expressed genes in vivo. Although previous methods for cDNA library synthesis (Sambrook et.al., "*Molecular Cloning*, 2nd Edition", pp8.1 1–8.35 (1989)) have succeeded in generating full-length cDNAs, the tedious procedure of reverse transcription, restriction, adaptor ligation and vector cloning usually fails to maintain the completeness of a cDNA library, resulting in loss of rare cDNAs when limited cells are used.

Prior art attempts at generation of complete cDNA library, such as U.S. Pat. No. 5,482,845 and U.S. Pat. No. 5,637,685 to Soares and U.S. Pat. No. 5,702,898 to Bonaldo, use reverse transcription and random priming polymerase chain reaction (RT-PCR) to construct normalized cDNA libraries for differential analysis (Patanjeli et.al., *Proc. Natl. Acad. Sci. USA* 88: 1943–1947 (1991)). In general, the amount of normalized cDNAs can be fully amplified by PCR to fulfill the requirement of completeness. However, the use of random-primer amplification greatly reduce the sequence integrity of the cDNAs. Because the normalized cDNA library usually lose part of sequences in the ends for cloning into a vector, this kind of low integrity may introduce significant difficulty in the sequence analysis, such as promoter detection. Moreover, the random amplification procedure increases non-specific contamination of primer dimers, resulting in false positive sequences in the cDNA library. Therefore, these disadvantages may even increase bias in experiments on minuscule samples, which require multiple amplification to bring up needed amount for analysis.

On the other hand, the generation of amplified antisense RNA (aRNA) has been developed to increase transcriptional copy of specific mRNAs from limited amount of cDNA library. The aRNA can be used for characterization of the expression pattern of certain gene transcripts in cells (O'Dell et.al., *BioTechniques* 25: 566–570 (1998)). By incorporating an oligo(dT)n primer coupled to a T7 RNA polymerase promoter sequence (oligo(dT)n-promoter) during reverse transcription (RT), the single copy mRNA can be amplified up to two thousand folds by aRNA amplification (Eberwine et.al , *Proc. Natl. Acad. Sci. USA* 89:3010–3014 (1992)). The aRNAs prepared from single live neuron has been reported to cover 50–75% of total intracellular mRNA population (Eberwine et.al, (1992); Crino et.al., *Proc. Natl. Acad. Sci. USA* 93: 14152–14157 (1996)), indicating that the prevention of mRNA degradation in cells is required to achieve 100% coverage of mRNA amplification. Although these aRNA synthesis methods lead to the identification of some abundant mRNA markers from single cells, the rare mRNAs may not be assessable by the current aRNA methods (O'Dell et.al. (1998)), resulting in low completeness of cDNA library.

In summary, it is desirable to have a fast, simple and specific method for generating complete full-length cDNA libraries from single cells, of which the results may be applied to screen differentially expressed genes, to test functional domain for gene regulation, and to design a therapy for diseases.

SUMMARY OF THE INVENTION

The present invention is a novel cDNA library synthesis method which generates a complete full-length cDNA library from as few as a cell.

Described in detail, a preferred embodiment of the present invention method includes the following steps:

a. providing a plurality of fixed cells, wherein said fixed cells inhibit intracellular mRNA degradation and also increase the permeabilisation of said cells for enzyme penetration;

b. incubating said fixed cells in a reverse transcription reaction with a plurality of oligo(dT)n-promoter sequences, wherein said reverse transcription reaction is reverse transcription of a plurality of mRNAs by using said oligo(dT)n-promoter as primer, to form a plurality of complementary DNAs from said mRNAs;

c. permitting said complementary DNAs in a cDNA tailing and double stranding reaction to form a plurality of poly(N)-tailed cDNAs, wherein said cDNA tailing and double-stranding reaction is a DNA polymerase and terminal transferase reaction capable of adding multiple copies of the same nucleotide to the tails of said complementary DNAs and then double-stranding said complementary DNAs from the tails;

d. incubating said poly(N)-tailed cDNAs in an in-vitro transcription reaction to generate a plurality of full-length aRNAs, wherein said in-vitro transcription reaction is an RNA polymerase reaction capable of synthesizing said full-length aRNAs from said poly(N)-tailed cDNAs;

e. incubating said full-length aRNAs in said reverse transcription reaction with a plurality of oligo(anti-poly(N))-promoter sequences to form a plurality of full-length cDNAs; wherein said oligo (anti-poly(N))-promoter sequences are complementary to the poly (N) tails of said poly(N)-tailed cDNAs; and f. amplifying said full-length cDNAs with a template-dependent extension of specific primers attached to the poly(dA)-tail and complementary promoter regions of said full-length cDNAs, and thereby providing a complete library enriched in full-length cDNAs from said fixed cells.

In one aspect of this embodiment, the further cycling steps of (d), (b), (d) and then (e) can be repeated at least one time on said full-length aRNA. According to another aspect of this preferred embodiment, the final nucleotide sequences are amplified, preferably, by PCR in the step (f).

The fixed cells can be prepared from cultured cells, frozen fresh tissues, fixed tissues or tissues in slides. To increase the production of said full-length aRNAs from said poly(N)-tailed cDNAs, the oligo(dT)n-promoter sequence is preferably added to the 5'-heads of said complementary DNA sequences in the step (b) for the in-cell transcription in the step (d). The promoter region of said oligo(dT)n-promoter can be recognized by an specific RNA polymerase and further transcribed into full-length aRNAs, such promoters including T3, T7, SP6, M13 and so on. Preferably, the incorporated nucleotide in said poly(N)-tailed cDNAs is either deoxyguanylate (dG) or deoxycytidylate (dC), and the average number of total incorporated nucleotides is larger than six; most preferably, the number is about twenty. Advantageously, the poly(dA)-tail and complementary promoter sequences in the ends of said full-length cDNAs can served as templates for the binding of specific primers during PCR amplification. The amplified full-length cDNA library is preferably cloned into a competent vector for further applications, such as overexpression assay, differential screening, functional detection and so on.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Figure 1:
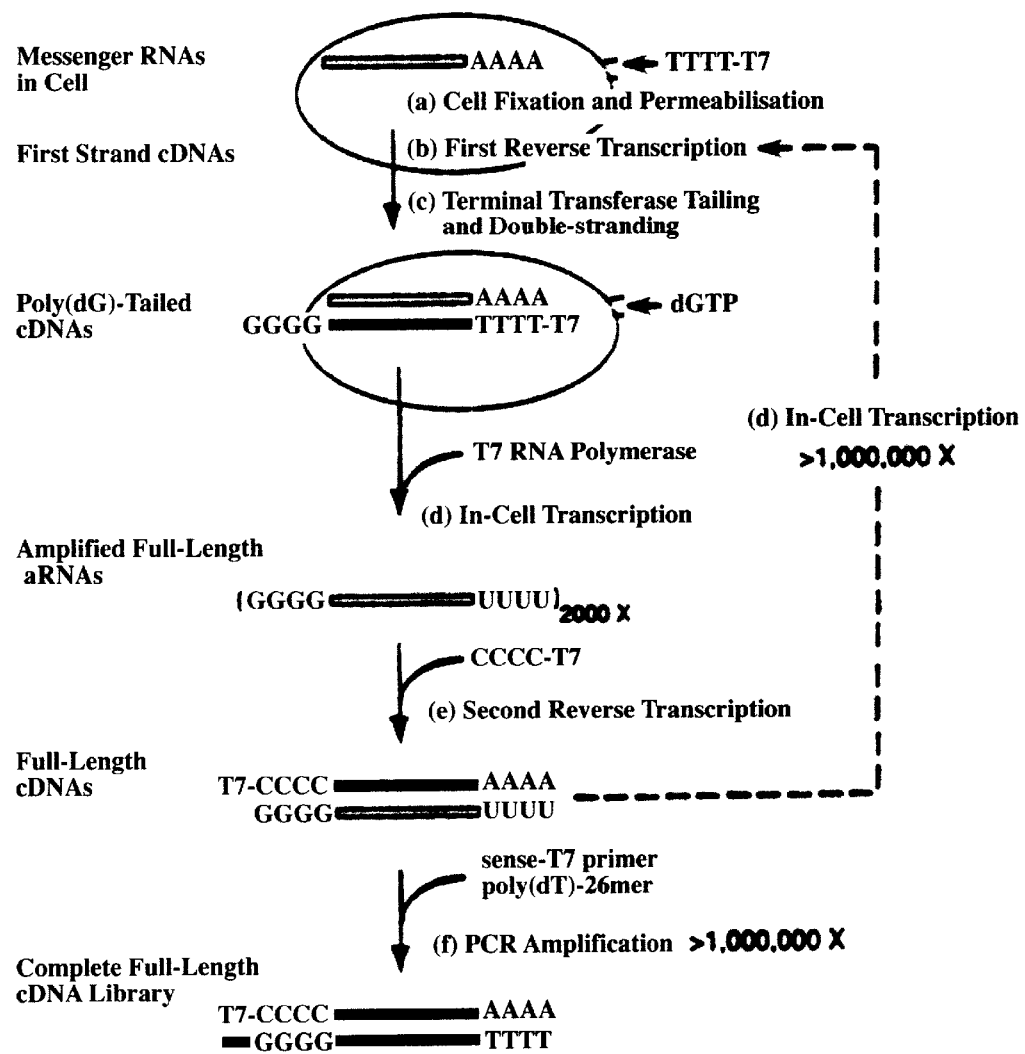
FIG. 1 is a flowchart of the preferred embodiment of the subject invention.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is directed to a novel method of full-length cDNA library synthesis from single cells, named "single-cell cDNA library amplification (SCLA)". This method is primarily designed for differential screening of tissue-specific gene expressions in cell level, cloning full-length sequences of unknown gene transcripts of interest, and preparing complete cDNA representatives for gene chip technology. The purpose of the SCLA relies on the repeating RT, in-cell transcription and PCR procedure to increase the population of cDNAs to two billion folds. The preferred version of the present invention is based on: 1) cell fixation to prevent mRNA degradation, 2) the first reverse transcription to incorporate promoter region into 5'-end of first strand cDNAs and then following an addition of poly-nucleotide (N) tail in the 3'-end for PCR, 3) in-cell transcription to increase mRNAs up to two thousand folds, 4) the second reverse transcription for next amplification cycle, and 5) PCR amplification to increase cDNAs again up to one million folds.

As used herein, the complementary DNA refers to a DNA sequence which is completely complementary to a mRNA sequence in an A–T and C–G composition. The poly(N)-tailed cDNA refers to a cDNA sequence containing full-length complementary mRNA sequence flanked by an oligo (dT)n-promoter sequence in the 5'-end and by a poly-nucleotide sequence in the 3'-end. And, the oligo(dT)n-promoter sequence refers to an RNA polymerase promoter sequence coupled with a poly-deoxythymidylate (dT) sequence in its 3'-end, of which the minimal number of linked dT is six; most preferably, the number is about twenty-six. The sense sequence refers to a nucleotide sequence which is in the same sequence and composition as its homologue in mRNAs, whereas the anti-sense sequence refers to a nucleotide sequence which is complementary to mRNA sequences Thus, the oligo (anti-poly(N))-promoter sequence refers to a nucleotide sequence which is complementary to the poly-nucleotide tail of said poly(N)-tailed cDNA and also linked with an RNA polymerase promoter in its 5'-end.

By improving and integrating two of current methods, in-cell RT-PCR (Embleton et.al, *Nucleic Acid Res.* 20: 3831–3837 (1992)) and aRNA amplification, we generate the in-cell transcription step of the present invention. This step is preferably performed after the first RT and before the second RT-PCR to form an amplification cycle for linear increase of total mRNA population. The advantages of incorporating the in-cell transcription of the first strand cDNAs into a traditional RT-PCR method are as follows: 1) single copy mRNAs can be amplified up to 2000 folds without mis-reading mistakes, 2) the mRNA amplification is linear and does not result in preferential amplification of abundant mRNA species, 3) the mRNA degradation is inhibited by using fixed cells, and 4) the final mRNA products are full-length and can be directly used to generate a complete cDNA library. In conjunction with a terminal tailing reaction, the cDNAs generated from above amplified mRNAs can be theoretically boosted over a billion folds by specific PCR.

In order to achieve the completeness of a full-length cDNA library, the procedure of the present invention is designed to generate 5'-RNA promoter head and 3'-poly(N) tail in the ends of the full-length cDNAs for final PCR amplification. As shown in FIG. 1, the 5'-RNA polymerase promoter region is incorporated during the first reverse hybridization step and then the 3'-poly(N) tail is added by a terminal transferase reaction. Preferably, the promoter is T7 RNA polymerase promoter and the poly(N) tail is poly-dG 20mer. This forms the binding templates in the both ends of the full-length cDNAs for high-fidelity PCR with specific primers, which is much more efficient and specific than a random priming amplification. Also, the long-length cDNAs can be fully amplified by using a long-expansion Taq-like polymerase in the PCR to achieve the integrity of sequence as large as 20 kb. In general, a complete cDNA library below 10 kb is good enough for most experimental analysis.

Although the preferred embodiment of the present invention starts from fixed cells; i.e., fixed cultured cells, frozen fresh tissues, fixed tissues or tissues in slides, the complete full-length cDNA library also can be made from extracted RNAs by the same procedure from step (b) to step (f) of this preferred embodiment with the difference of using total RNAs/mRNAs instead of fixed cells. Since this formed cDNAs are of full-length and carry RNA promoter regions for in vitro/vivo expression, the transfection of certain cDNA representative can be directly performed after cloning into a competent vector. Alternatively, the labeling of the cDNAs can be accomplished by incorporation of labeled nucleotides or analogs during tailing reaction, while that of the amplified mRNAs is completed during transcription of the poly(N)-tailed cDNAs. The labeled nucleotide sequences will be served as probes in a variety of experimental applications, such as Northern blots, Southern blots, in-situ hybridization and antisense knock-out assay.

The present invention will be very useful in preparing complete full-length cDNA libraries for future gene chip technology. Because the present invention is capable of generating a complete repertoire of full-length cDNAs from single cells, the tissue-specific cDNA library based on a special cell type can be formed and transferred onto a filter, membrane or chip for preserving these genetic information. As we all have different genetic information from a variety of major tissues and organs, the cDNA-encoded gene chips may function as an individual source for differential screening, pathological diagnosis, physiological prognosis and genetic identification. This kind of approach will become more and more important following the completion of human genome project in the year 2003. Examples as mentioned here will be developed into continuity in part of the present invention and is not intended in any way to limit the broad features or principles of the present invention.

Although certain preferred embodiments of the present invention have been described, the spirit and scope of the invention is by no means restricted to what is described above. For example, within the general framework of: a) one or more specific primers for RT and PCR; b) one or more RNA promoters for transcription of cDNAs; c) six or more deoxythymidylates linked in an oligo(dT)n-promoter primer; d) seven or more same nucleotides added to the 3'-end of the first strand cDNAs ; e) one or more rounds of the steps (b) to (e) as shown in FIG. 1, there is a very large number of permutations and combinations possible, all of which are within the scope of the present invention.

EXAMPLE 1

Cell Fixation and Permeabilisation

LNCaP cells, a prostate cancer cell line, were grown in RPMI 1640 medium supplemented with 2% fetal calf serum. One 70% full of cells cultured in 60 mm dish were trypsinized, collected and washed three times in 5 ml phosphate buffered saline (PBS, pH 7.2) at room temperature, then suspended in 1 ml of ice-cold 10% formaldehyde solution in 0.15M NaCl. After one hour incubation on ice with occasional agitation, the cells were centrifuged at 13,000 rpm for 2 min and wash three times in ice-cold PBS with vigorous pipetting. The collected cells were resuspended in 0.5% Nonidet P40 (NP40, B.D.H.) and incubated for one hour with frequent agitation. After that, three washes were given to cells in ice-cold PBS containing 0.1M glycine and the cells were resuspended in 1 ml of the same buffer with vigorous pipetting in order to be evenly separated into small aliquots and stored at −70° C. for up to a month.

EXAMPLE 2

In-Cell Reverse Transcription and Poly-(N) Tailing of cDNAs

For reverse transcription of mRNAs in cells, twenty of the fixed cells were thawed, resuspended in 20 μl of ddH$_2$O, heated to 65° C. for 3 min and then cooled on ice. A 50 μl RT reaction was prepared, comprising 5 μl of 10x in-cell RT buffer (1.2M KCl, 0.5M Tris-HCl, 80 mM MgCl$_2$, 10 mM dithiothreitol, pH 8.1 at 42° C.), 5 μl of 5 mM dNTPs, 25 pmol oligo(dT)n-T7 promoter (SEQ ID NO. 1), 80U RNase inhibitor and above cold cells. After reverse transcriptase (40U) was added, the RT reaction was mixed and incubated at 55° C. for three hours, and then the cells were washed once with PBS and resuspended in a 50 μl tailing reaction, comprising 2 mM dGTP, 10 μl of 5x tailing buffer (250 mM KCl, 50 mM Tris-HCl, 7.5 mM MgCl$_2$, pH 8.3 at 20° C.). The tailing reaction was heated at 94° C. for 3 min and then chilled in ice for mixing with terminal transferase (20U), following further incubation at 37° C. for 20 min. Final reaction was stopped at 94° C. for 3 min and chilled in ice immediately, and this formed said poly(N)-tailed cDNAs.

EXAMPLE 3

Single-Cell mRNA Amplification

To increase the intracellular copies of whole mRNAs, the T7 promoter region of a poly(N)-tailed cDNA was served as a coding strand for the amplification by T7 RNA polymerase (Eberwine et.al. (1992)). As few as one cell in 5 μl of above tailing reaction can be used to accomplish full-length aRNA amplification. An in-cell transcription reaction was prepared on ice, containing 25 pmol poly(dC)-20mer primer, 1 mM dNTPs, Pwo DNA polymerase (5U), 5 μl of 10x Transcription buffer (Boehringer Mannheim), 2 mM NTPs and T7 RNA polymerase (2000U). The hybridization of 20mer primer to the poly(N)-tailed cDNAs was incubated at 65° C. for 5 min to complete second strand cDNA synthesis and then RNA polymerase was added to start transcription. After four hour incubation at 37° C., the cDNA transcripts were isolated from both cells and supernatant, and can be directly used in following reverse transcription. The reaction was finally stopped at 94° C. for 3 min and chilled in ice.

EXAMPLE 4

In Vitro Reverse Transcription and PCR Amplification

Figure 2:
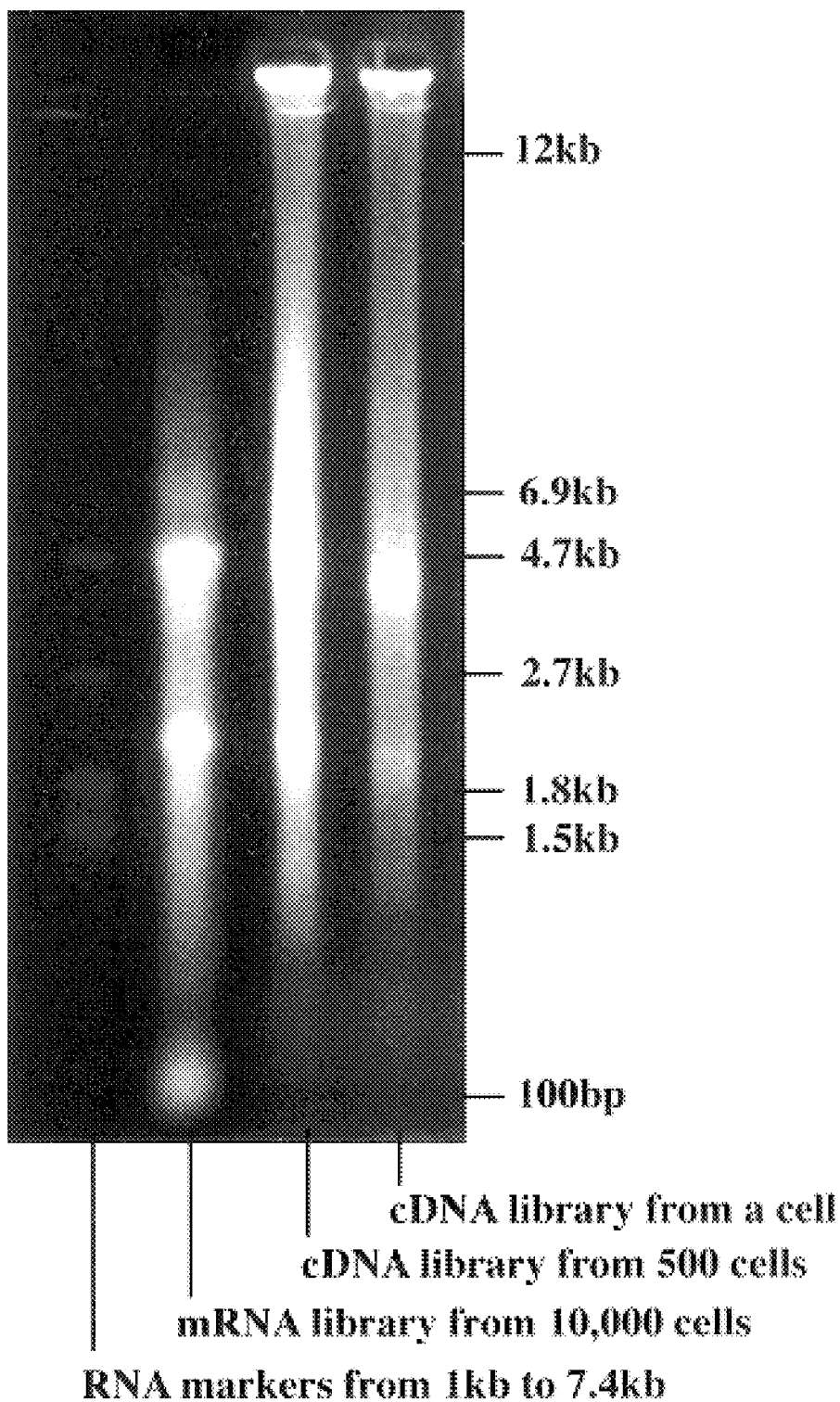
FIG. 2 is the result of example 4 of the subject invention.

A 50 μl RT reaction was prepared, comprising 5 μl of 10x RT buffer (300 mM KCl, 0.5M Tris-HCl, 80 mM MgCl$_2$, 10 mM dithiothreitol, pH 8.3 at 20° C.), 5 μl of 5 mM dNTPs, 25 pmol oligo(dC)n-T7 promoter (SEQ ID NO. 3), 80U RNase inhibitor, ddH$_2$O and 5 μl of above aRNA containing supernatant. After reverse transcriptase (40U) was added, the RT reaction was vortexed and incubated at 55° C. for three hours. The resulting products of RT can be directly used in following PCR reaction (50 µl), comprising 5 µl of 10x PCR buffer (Boehringer Mannheim), 5 µl of 2 mM dNTPs, 25 pmol T7-20mer primer 25 pmol poly(dT)-26mer primer (SEQ ID NO. 4), ddH$_2$O, 5 µl of above RT product and 3U of Taq/Pwo long-extension DNA polymerase. The PCR reaction was subjected to thirty cycles of denaturation at 95° C. for 1 min, annealing at 55° C. for 1 min and extension at 72° C. for 3 min. The quality of final amplified cDNA library (20 µl) was assessed on a 1% formaldehyde-agarose gel, ranging from 100 bp to above 12 kb (FIG. 2). We also have successfully generated a p16 and a p53 probe from the final cDNA library by using primer-specific PCR.

The present invention has been described with reference to particular preferred embodiments; however, the scope of this invention is defined by the attached claims and should be constructed to include reasonable equivalents.

Defined in detail, the present invention is a method of generating a complete full-length cDNA library from single cells, comprising the steps of:

a. providing a plurality of fixed cells, wherein said fixed cells inhibit intracellular mRNA degradation and also increase the permeabilisation of said cells for enzyme penetration;

b. incubating said fixed cells in a reverse transcription reaction with a plurality of oligo(dT)n-promoter sequences, wherein said reverse transcription reaction is reverse transcription of a plurality of mRNAs by using said oligo(dT)n-promoter as primer, to form a plurality of complementary DNAs from said mRNAs;

c. permitting said complementary DNAs in a cDNA tailing and double-stranding reaction to form a plurality of poly(N)-tailed cDNAs, wherein said cDNA tailing and double-stranding reaction is a terminal transferase reaction capable of adding multiple copies of the same nucleotide to the tails of said complementary DNAs;

d. incubating said poly(N)-tailed cDNAs in an in-vitro transcription reaction to generate a plurality of full-length RNAs, wherein said in-vitro transcription reaction is an RNA polymerase reaction capable of synthesizing said full-length RNAs from said poly(N)-tailed cDNAs;

e. incubating said full-length RNAs in said reverse transcription reaction with a plurality of oligo (anti-poly (N))-promoter sequences to form a plurality of full-length cDNAs; wherein said oligo (anti-poly(N))-promoter sequences are complementary to the poly(N) tails of said poly(N)-tailed cDNAs and f. amplifying said full-length cDNAs with a template-dependent extension of specific primers attached to the poly(dA)-tail and complementary promoter regions of said full-length cDNAs, and thereby providing a complete library enriched in full-length cDNAs from said fixed cells.

Defined broadly, the present invention is a method of performing improved full-length cDNA library synthesis, comprising the steps of:

a. preventing a plurality of mRNAs from degradation, wherein said mRNAs are preserved to be intact in cells;

b. generating a plurality of complementary DNAs from said mRNAs, wherein said complementary DNAs are reverse-transcribed from said mRNAs;

c. permitting said complementary DNAs to form a plurality of poly(N)-tailed cDNAs, wherein said poly(N)-tailed cDNA contains a full-length complementary DNA sequence flanked with an RNA polymerase promoter in the 5'-end and a poly-nucleotide tail in the 3'-end; and d. amplifying said poly(N)-tailed cDNAs by a plurality of promoter- and tail-dependent extension systems, and thereby providing a complete library of full-length cDNAs from said mRNAs.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to shown all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What we claim is:

1. A method of generating a complete full-length cDNA library from single cells, comprising the steps of:
   a. providing a plurality of fixed cells, wherein said fixed cells inhibit intracellular messenger RNA degradation and also increase the permeabilisation of said cells for enzyme penetration;
   b. incubating said fixed cells in a reverse transcription reaction with a plurality of oligo(dT)n-promoter sequences, wherein said reverse transcription reaction is reverse transcription of a plurality of messenger RNAs by using said oligo(dT)n-promoter as primer, to form a plurality of complementary DNAs from said messenger RNAs;
   c. permitting said complementary DNAs in a cDNA tailing and double-stranding reaction to form a plurality of poly(N)-tailed cDNAs, wherein said cDNA tailing and double-stranding reaction is a DNA polymerase and terminal transferase reaction capable of adding multiple copies of the same nucleotide to the tails of said complementary DNAs and then double-stranding said complementary DNAs from the tails;
   d. incubating said poly(N)-tailed cDNAs in an in-vitro transcription reaction to generate a plurality of full-length aRNAs, wherein said in-vitro transcription reaction is RNA's polymerase reaction capable of synthesizing said full-length RNA's from said poly(N)-tailed cDNAs;
   e. incubating said full-length aRNAs in said reverse transcription reaction with a plurality of oligo (anti-poly(N))-promoter sequences to form a plurality of full-length cDNAs; wherein said oligo (anti-poly(N))-promoter sequences are complementary to the poly(N) tails of said poly(N)-tailed cDNAs and
   f. amplifying said full-length cDNAs with a template-dependent extension of specific primers attached to the poly (dA)-tail and complementary promoter regions of said full-length cDNAs, and thereby providing a complete library enriched in full-length cDNAs from said fixed cells.

2. The method as defined in claim 1, further comprising the step of repeating steps of (b) through (e) on said full-length RNAs at least one time.

3. The method as defined in claim 1, further comprising the step of cloning said amplified full-length cDNA library into competent vectors after the step (f).

4. The method as defined in claim 1, further comprising the step of hybridization of said oligo(dT)n-promoter sequences to said messenger RNAs in the step (b).

5. The method as defined in claim 4, wherein said oligo(dT)n-promoter sequence is a poly(dT) primer coupled to an RNA polymerase promoter in the 5'-end of said poly(dT) primer, of which the number of deoxythymidylate (dT) is larger than six nucleotides.

6. The method as defined in claim 5, wherein said RNA polymerase promoter is T3 RNA polymerase promoter.

7. The method as defined in claim 5, wherein said RNA polymerase promoter is T7 RNA polymerase promoter.

8. The method as defined in claim 5, wherein said RNA polymerase promoter is SP6 RNA polymerase promoter.

9. The method as defined in claim 5, wherein said RNA polymerase promoter is M13 RNA polymerase promoter.

10. The method as defined in claim 1, wherein said reverse transcription reaction is performed with AMV reverse transcriptase.

11. The method as defined in claim 1, wherein said reverse transcription reaction is performed with MMLV reverse transcriptase.

12. The method as defined in claim 1, wherein said cDNA tailing and double stranding reaction is performed with terminal transferase.

13. The method as defined in claim 1, wherein said in-vitro transcription reaction is performed with T3 RNA polymerase.

14. The method as defined in claim 1, wherein said in-vitro transcription reaction is performed with T7 RNA polymerase.

15. The method as defined in claim 1, wherein said in-vitro transcription reaction is performed with SP6 RNA polymerase.

16. The method as defined in claim 1, wherein said in-vitro transcription reaction is performed with M13 RNA polymerase.

17. The method as defined in claim 1, wherein said template-dependent extension is a polymerase chain reaction.

18. The method as defined in claim 1, wherein said poly(N)-tailed cDNAs are terminally added by multiple copies of the same nucleotide in the 3'-end.

19. The method as defined in claim 18, wherein said same nucleotide is deoxyguanylate.

20. The method as defined in claim 18, wherein said same nucleotide is deoxycytidylate.

21. The method as defined in claim 18, wherein said same nucleotide is deoxyadenylate.

22. The method as defined in claim 18, wherein said same nucleotide is deoxythymidylate.

23. The method as defined in claim 18, wherein said same nucleotide is deoxyuridylate.

24. A method of performing improved full-length cDNA library synthesis, comprising the steps of:
   a. preventing a plurality of messenger RNAs from degradation, wherein said messenger RNAs are preserved to be intact in cells;
   b. generating a plurality of complementary DNAs from said messenger RNAs, wherein said complementary DNAs are reverse-transcribed from said messenger RNAs;
   c. permitting said complementary DNAs to form a plurality of poly(N)-tailed cDNAs, wherein said poly(N)-tailed cDNA contains a full-length complementary DNA sequence flanked with an RNA polymerase promoter in the 5'-end and a poly-nucleotide tail in the 3'-end; and
   d. amplifying said poly(N)-tailed cDNAs by a plurality of promoter- and tail-dependent extension systems, and thereby providing a complete library of full-length cDNAs from said messenger RNAs.

25. The method as defined in claim 24, further comprising the step of cloning said full-length cDNA library into competent vectors after the step (d).

26. The method as defined in claim 24, wherein said RNA polymerase promoter is T3 RNA polymerase promoter.

27. The method as defined in claim 24, wherein said RNA polymerase promoter is T7 RNA polymerase promoter.

28. The method as defined in claim 24, wherein said RNA polymerase promoter is SP6 RNA polymerase promoter.

29. The method as defined in claim 24, wherein said RNA polymerase promoter is M13 RNA polymerase promoter.

30. The method as defined in claim 24, wherein said messenger RNAs are protected by fixation.

31. The method as defined in claim 24, wherein said messenger RNAs are protected by RNase inhibitors.

32. The method as defined in claim 24, wherein said complementary DNAs are generated by reverse transcriptase with oligo(dT)n-promoter sequences.

33. The method as defined in claim 24, wherein said poly(N)-tailed cDNAs are formed with terminal transferase.

34. The method as defined in claim 24, wherein said poly(N)-tailed cDNAs are amplified with T3 RNA polymerase and reverse transcriptase.

35. The method as defined in claim 24, wherein said poly(N)-tailed cDNAs are amplified with T7 RNA polymerase and reverse transcriptase.

36. The method as defined in claim 24, wherein said poly(N)-tailed cDNAs are amplified with SP6 RNA polymerase and reverse transcriptase.

37. The method as defined in claim 24, wherein said poly(N)-tailed cDNAs are amplified with M13 RNA polymerase and reverse transcriptase.

38. The method as defined in claim 24, wherein said promoter- and tail-dependent extension system is a procedure of transcription, reverse transcription and polymerase chain reaction.

39. The method as defined in claim 24, wherein said poly(N)-tailed cDNAs contain multiple copies of the same nucleotide in the 3'-end.

40. The method as defined in claim 39, wherein said same nucleotide is deoxyguanylate.

41. The method as defined in claim 39, wherein said same nucleotide is deoxycytidylate.

42. The method as defined in claim 39, wherein said same nucleotide is deoxyadenylate.

43. The method as defined in claim 39, wherein said same nucleotide is deoxythymidylate.

44. The method as defined in claim 39, wherein said same nucleotide is deoxyuridylate.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 59 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic"

(iii) HYPOTHETICAL: NO (iv) ANTI-SENSE: NO (xi) SEQUENCE DESCRIPTION: SEQ ID NO: 1:

AAGCTTAGAT ATCTAATACG ACTCACTATA GGGAATTTTT TTTTTTTTTT TTTTTTTTT        59

(2) INFORMATION FOR SEQ ID NO: 2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic"

(iii) HYPOTHETICAL: NO (iv) ANTI-SENSE: NO (xi) SEQUENCE DESCRIPTION: SEQ ID NO: 2:

CCCCCCCCCC CCCCCCCCCC                                                  20

(2) INFORMATION FOR SEQ ID NO: 3:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic"

(iii) HYPOTHETICAL: NO (iv) ANTI-SENSE: NO (xi) SEQUENCE DESCRIPTION: SEQ ID NO: 3:

AAGCTTAGAT ATCTAATACG ACTCACTATA GGGAACCCCC CCCCCCC                    47

(2) INFORMATION FOR SEQ ID NO: 4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic"

(iii) HYPOTHETICAL: NO (iv) ANTI-SENSE: NO (xi) SEQUENCE DESCRIPTION: SEQ ID NO: 4:

CTAATACGAC TCACTATAGG                                                  20

(2) INFORMATION FOR SEQ ID NO: 5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic"

(iii) HYPOTHETICAL: NO

-continued (iv) ANTI-SENSE: NO (xi) SEQUENCE DESCRIPTION: SEQ ID NO: 5:

TTTTTTTTTT TTTTTTTTTT TTTTTT     26